(12) United States Patent
Sun et al.

(10) Patent No.: US 7,192,703 B2
(45) Date of Patent: Mar. 20, 2007

(54) BIOMOLECULE ANALYSIS BY ROLLING CIRCLE AMPLIFICATION AND SERS DETECTION

(75) Inventors: Lei Sun, Santa Clara, CA (US); Xing Su, Cupertino, CA (US)

(73) Assignee: Intel Corporation, Inc., Santa Clara, CA (US)

( * ) Notice: Subject to any disclaimer, the term of this patent is extended or adjusted under 35 U.S.C. 154(b) by 606 days.

(21) Appl. No.: 10/367,071

(22) Filed: Feb. 14, 2003

(65) Prior Publication Data

US 2004/0161750 A1 Aug. 19, 2004

(51) Int. Cl.
*C12Q 1/68* (2006.01)
*C12P 19/34* (2006.01)

(52) U.S. Cl. .......................................... 435/6; 435/91.2
(58) Field of Classification Search .................... 435/6, 435/91.2
See application file for complete search history.

(56) References Cited

U.S. PATENT DOCUMENTS

| | | | |
|---|---|---|---|
| 4,962,037 | A | 10/1990 | Jett et al. |
| 5,306,403 | A | 4/1994 | Vo-Dinh |
| 5,405,747 | A | 4/1995 | Jett et al. |
| 6,002,471 | A | 12/1999 | Quake |
| 6,043,034 | A * | 3/2000 | Takama et al. ............... 435/6 |
| 6,054,274 | A | 4/2000 | Sampson et al. |
| 6,054,495 | A | 4/2000 | Markowitz et al. |
| 6,127,120 | A | 10/2000 | Graham et al. |
| 6,136,543 | A | 10/2000 | Anazawa et al. |
| 6,149,868 | A | 11/2000 | Natan et al. |
| 6,174,677 | B1 | 1/2001 | Vo-Dinh |
| 6,180,415 | B1 * | 1/2001 | Schultz et al. .............. 436/518 |
| 6,210,896 | B1 | 4/2001 | Chan |
| 6,291,187 | B1 | 9/2001 | Kingsmore et al. |
| 6,323,009 | B1 | 11/2001 | Lasken et al. |
| 6,344,329 | B1 | 2/2002 | Lizardi |
| 6,368,801 | B1 | 4/2002 | Faruqi |
| 6,376,177 | B1 | 4/2002 | Poponin |
| 6,514,767 | B1 | 2/2003 | Natan ........................ 436/166 |

FOREIGN PATENT DOCUMENTS

| | | |
|---|---|---|
| WO | WO00/68434 | 11/2000 |
| WO | WO01/88190 | 11/2001 |
| WO | WO01/97616 | 12/2001 |
| WO | WO02/074988 | 9/2002 |

OTHER PUBLICATIONS

Doering, et al., "Spectroscopic Tags Using Dye-Embedded Nanoparticles and Surface - Enhanced Raman Scattering", *Analytical Chemistry*, :5-9.
Mulvaney, et al., "Glass-Coated, Analyte-Tagged Nanoparticles: A New Tagging System Based on *Detection* with Surface-Enhanced Raman Scattering", *Am Chem Soc.* 19:4784-4790 (2003).
Banér, et al., "Signal Amplification of Padlock Probes by Rolling Circle Replication," *Nucleic Acids Research*, 26:5073-5078, 1998.
Dean, et al., "Rapid Amplification of Plasmid and Phage DNA Using Phi29 DNA Polymerase and Multiply-Primed Rolling Circle Amplification," *Genome Res.*, 11:1095-1099, 2001.
Faruqi, et al., "High-Throughput Genotyping of Single Nucleotide Polymorphisms with Rolling Circle Amplification," *BMC Genomics*, 2:4, 2000.
Feldheim, "Assembly of Metal Nanoparticle Arrays Using Molecular Bridges," *The Electrochemical Society Interface*, Fall, 2001, pp. 22-25.
Jin, et al., "Photoinduced Conversion of Silver Nanospheres to Nanoprisms," *Science*, 294:1901, 2001.
Keren, et al., "Sequence-Specific Molecular Lithography on Signal DNA Molecules," *Science* 297:72-75, 2002.
Lee, et al., "Adsorption and Surface-Enchanced Raman of Dyes on Silver and Gold Sols," *J. Phys. Chem.* 86:3391-3395, 1982.
Liu, et al., "Positioning Protein Molecules on Surfaces: A Nanoengineering Approach to Supramolecular Chemistry," *Proc. Natl. Acad. Sci. USA*, 99:5165-70, 2002.

(Continued)

*Primary Examiner*—Kenneth R. Horlick
*Assistant Examiner*—Joyce Tung
(74) *Attorney, Agent, or Firm*—Morrison & Foerster LLP (57) ABSTRACT

The present methods, compositions and systems are concerned with biomolecule 130 detection, identification and/or quantification by rolling circle amplification (RCA) and Raman detection. In particular embodiments of the invention, the RCA is exponential RCA or linear RCA. In some embodiments of the invention, the Raman detection is SERS or SERRS. The circular DNA template 150, 210, 310 to be amplified may comprise one or more polythymidine 320 residues, resulting in amplification products 170, 230, 250, 330, 410 containing multiple polyadenylate 340, 420 residues. The polyadenylates 340, 420 may be directly detected by Raman detection. Alternatively, one or more Raman labels may be incorporated into the amplification products 170, 230, 250, 330, 410 to facilitate Raman detection. Because of the amplification produced by LRCA or ERCA and the enhanced Raman signal produced by multiple polyadenylates 340, 420 and/or Raman labels, detection of single copy biomolecules 130 is feasible using the disclosed methods, compositions and/or systems.

20 Claims, 7 Drawing Sheets

OTHER PUBLICATIONS

Lizardi, et al., "Mutation Detection and Single-Molecule Counting Using Isothermal Rolling-Circle Amplification," *Nature Genetics* 19:225, 1998.

Nallur, et al., "Signal Amplification by Rolling Circle Amplification on DNA Microarrays," *Nucl. Acids Res.* 29:e118, 2001.

Schweitzer, et al., "Immunosassays with Rolling Circle DNA Amplification: A Versatile Platform for Ultrasensitive Antigen Detection," *Proc. Natl. Acad. Sci. USA* 97:10113-119, 2000.

Schweitzer, et al., "Multiplexed Protein Profiling on Microarrays by Rolling-Circle Amplification," *Nature Biotech.* 20:359-365, 2002.

* cited by examiner

BIOMOLECULE ANALYSIS BY ROLLING CIRCLE AMPLIFICATION AND SERS DETECTION

BACKGROUND

1. Field

Embodiments of the invention relate to the field of biomolecule 130 analysis. In particular, to systems, compositions and methods relating to rolling circle amplification and Raman detection of biomolecules 130.

2. Background

The sensitive and accurate detection, identification and/or quantification of low concentrations of biomolecules, such as proteins, peptides, oligonucleotides, nucleic acids, lipids, polysaccharides, hormones, neurotransmitters, metabolites, etc. has proven to be an elusive goal, with widespread potential uses in medical diagnostics, pathology, toxicology, epidemiology, biological warfare, environmental sampling, forensics and numerous other fields. Present detection methods typically involve detection of a fluorescently tagged capture molecule or ligand that can bind to the target biomolecule. Fluorescently tagged antibodies or probe oligonucleotides are typically used to bind to and detect target proteins or nucleic acids, respectively. Cross-reactivity and non-specific binding may complicate fluorescent detection of biomolecules in complex samples. Even where high specificity is obtained, the sensitivity of fluorescent detection is often insufficient to identify low concentrations of biomolecules. This is particularly true when the biomolecule to be detected is present at low concentrations in a complex mixture of other molecules, where interference, fluorescence quenching and high background fluorescence may all act to obscure or diminish the signal from the target biomolecule.

Other detection modalities have been attempted for biomolecule detection, such as Raman spectroscopy and/or surface plasmon resonance. When light passes through a tangible medium, a certain amount becomes diverted from its original direction, a phenomenon known as Raman scattering. Some of the scattered light also differs in frequency from the original excitatory light, due to the absorption of light and excitation of electrons to a higher energy state, followed by light emission at a different wavelength. The wavelengths of the Raman emission spectrum are characteristic of the chemical composition and structure of the light absorbing molecules in a sample, while the intensity of light scattering is dependent on the concentration of molecules in the sample.

The probability of Raman interaction occurring between an excitatory light beam and an individual molecule in a sample is very low, resulting in a low sensitivity and limited applicability of Raman analysis. It has been observed that molecules near roughened silver surfaces show enhanced Raman scattering of as much as six to seven orders of magnitude. This surface enhanced Raman spectroscopy (SERS) effect is related to the phenomenon of plasmon resonance, wherein metal nanoparticles exhibit a pronounced optical resonance in response to incident electromagnetic radiation, due to the collective coupling of conduction electrons in the metal. In essence, nanoparticles of gold, silver, copper and certain other metals can function as miniature "antenna" to enhance the localized effects of electromagnetic radiation. Molecules located in the vicinity of such particles exhibit a much greater sensitivity for Raman spectroscopic analysis.

Attempts have been made to exploit SERS for biomolecule detection and analysis, typically by coating metal nanoparticles or fabricating rough metal films on a substrate and then applying a sample to the metal-coated substrate. However, the number of metal particles that can be deposited on a planar substrate is limited, producing a relatively low enhancement factor for SERS and related Raman techniques utilizing such substrates. Thus, present methods of SERS detection do not exhibit sufficient sensitivity to detect low concentrations of biomolecules. A need exists for highly sensitive and specific methods of biomolecule detection.

BRIEF DESCRIPTION OF THE DRAWINGS

The following drawings form part of the present specification and are included to further demonstrate certain embodiments of the invention. The embodiments may be better understood by reference to one or more of these drawings in combination with the detailed description of specific embodiments presented herein.

DESCRIPTION OF ILLUSTRATIVE EMBODIMENTS

Definitions

As used herein, "a" or "an" may mean one or more than one of an item.

"Nucleic acid" encompasses DNA (deoxyribonucleic acid), RNA (ribonucleic acid), single-stranded, double-stranded or triple stranded and any chemical modifications thereof. The term also encompasses any known nucleic acid analog, including but not limited to peptide nucleic acids (PNA), nucleic acid analog peptides (NAAP) and locked nucleic acids (LNA). A "nucleic acid" may be of almost any length, from oligonucleotides of two or more bases up to a full-length chromosomal DNA molecule. "Nucleic acids" include, but are not limited to, oligonucleotides and polynucleotides. Although nucleotide residues in naturally occurring nucleic acids are typically joined together by phosphodiester bonds, within the scope of the disclosed methods nucleotide residues may be joined by phosphodiester bonds or by any other type of known covalent attachment.

The terms "protein" "polypeptide" and "peptide" are used interchangeably herein to refer to polymeric molecules, assembled from naturally occurring amino acids, non-naturally occurring amino acids, amino acid analogues and/or amino acid derivatives. The distinction between the terms is primarily one of length and the skilled artisan will realize that where the following disclosure refers to proteins, polypeptides or peptides, the terms encompass polymers, of any length. Although amino acid residues in naturally occurring proteins, polypeptides and peptides are typically joined together by peptide bonds, within the scope of the disclosed methods amino acid residues may be joined by peptide bonds or by any other type of known covalent attachment.

As used herein, the terms "biomolecule" 130, "analyte" 130 and "target" 130 refer to any molecule or aggregate of molecules of interest for detection in a biological sample. Non-limiting examples of biomolecules 130 include a protein, peptide, amino acid, nucleic acid, oligonucleotide, nucleotide, nucleoside, carbohydrate, polysaccharide, glycoprotein, lipid, hormone, growth factor, cytokine, neurotransmitter, receptor, enzyme, antigen, allergen, antibody 120, metabolite, cofactor, nutrient, toxin, poison, biowarfare agent, biohazardous agent, infectious agent, prion and vitamin. "Biomolecules" 130 are not limited to single molecules, but may also comprise complex aggregates, such as a virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen or cell.

A "biological sample" is any sample obtained or obtainable from a biological source and/or including material from a biological source. A "biological sample" includes, but is not limited to blood, lymph, cerebrospinal fluid, sputum, semen, urine, feces, hair follicles, lachrymal fluid, epithelial scrapings, a cell sample, a tissue sample, an organ sample, a biopsy sample, cultured cells, as well as extracts and/or homogenates of cells, tissues or organs, etc.

Rolling Circle Amplification

In various embodiments of the invention, the disclosed methods may comprise rolling circle amplification (RCA). Techniques for rolling circle amplification are known in the art (see, e.g., Banér et al, *Nucleic Acids Research*, 26:5073–5078, 1998; Lizardi et al., *Nature Genetics* 19:226, 1998; Schweitzer et al. *Proc. Natl. Acad. Sci. USA* 97:10113–119, 2000; Faruqi et al., *BMC Genomics* 2:4, 2000; Nallur et al., *Nucl. Acids Res.* 29:e118, 2001; Dean et al. *Genome Res.* 11:1095–1099, 2001; Schweitzer et al., *Nature Biotech.* 20:359–365, 2002; U.S. Pat. Nos. 6,054, 274, 6,291,187, 6,323,009, 6,344,329 and 6,368,801). Several different variants of RCA are known, including linear RCA (LRCA) and exponential RCA (ERCA).

LRCA

Figure 1:
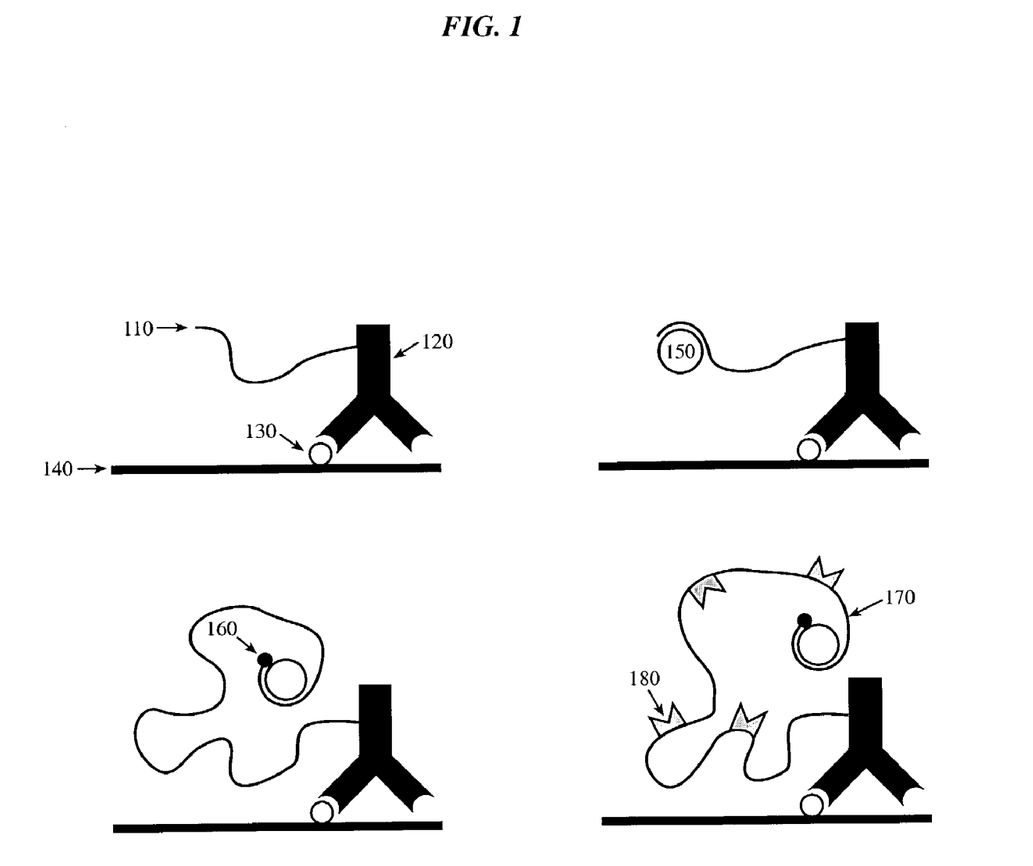
FIG. 1 illustrates a method of linear rolling circle amplification (LRCA). The particular type of assay disclosed is an immunoRCA (rolling circle amplification) assay, using an antibody 120 conjugated to an oligonucleotide primer 110. The oligonucleotide primer 110 can hybridize to a single-stranded circular nucleic acid template 150 and prime the RCA process.

FIG. 1 illustrates the general protocol of LRCA. In this example, a primer 110 for RCA is conjugated to an antibody 120 that can bind to and recognize a biomolecule 130. Thus, this RCA variant is sometimes referred to as immunoRCA (Schweitzer et al., 2000). The biomolecule 130 may be attached to a substrate 140, allowing localization and detection of the signal. A single-stranded, circular DNA template 150 with sequences complementary to the primer 110 is allowed to hybridize to the primer 110. Upon addition of a DNA polymerase 160, in the presence of appropriate dNTP (deoxynucleoside triphosphate) precursors and other cofactors, the primer 110 strand is elongated. Because the template 150 sequence is circular, multiple copies of the template 150 sequence will be replicated and attached to the primer 110.

A variety of detection techniques are available to identify the LRCA amplification product 170. As shown in FIG. 1, a common technique is to add a fluorescently tagged oligonucleotide probe 180 that can hybridize specifically to a sequence internal to the circular DNA template 150. A probe molecule 180 can bind to each copy of the template 150 sequence in the amplification product 170, allowing a multiplication of the fluorescent signal detectable from the biomolecule 130-antibody 120 complex. In general, LRCA provides about a four order of magnitude ($10^4$) signal amplification to facilitate detection of low-abundance target biomolecules 130.

ERCA

For detection of target biomolecules 130 in very low abundance, the LRCA protocol may not provide sufficient signal amplification for sensitive and reliable detection. Another variant of RCA—exponential RCA (ERCA)—was developed to provide for additional signal amplification with the rolling circle technique (FIG. 2).

Figure 2:
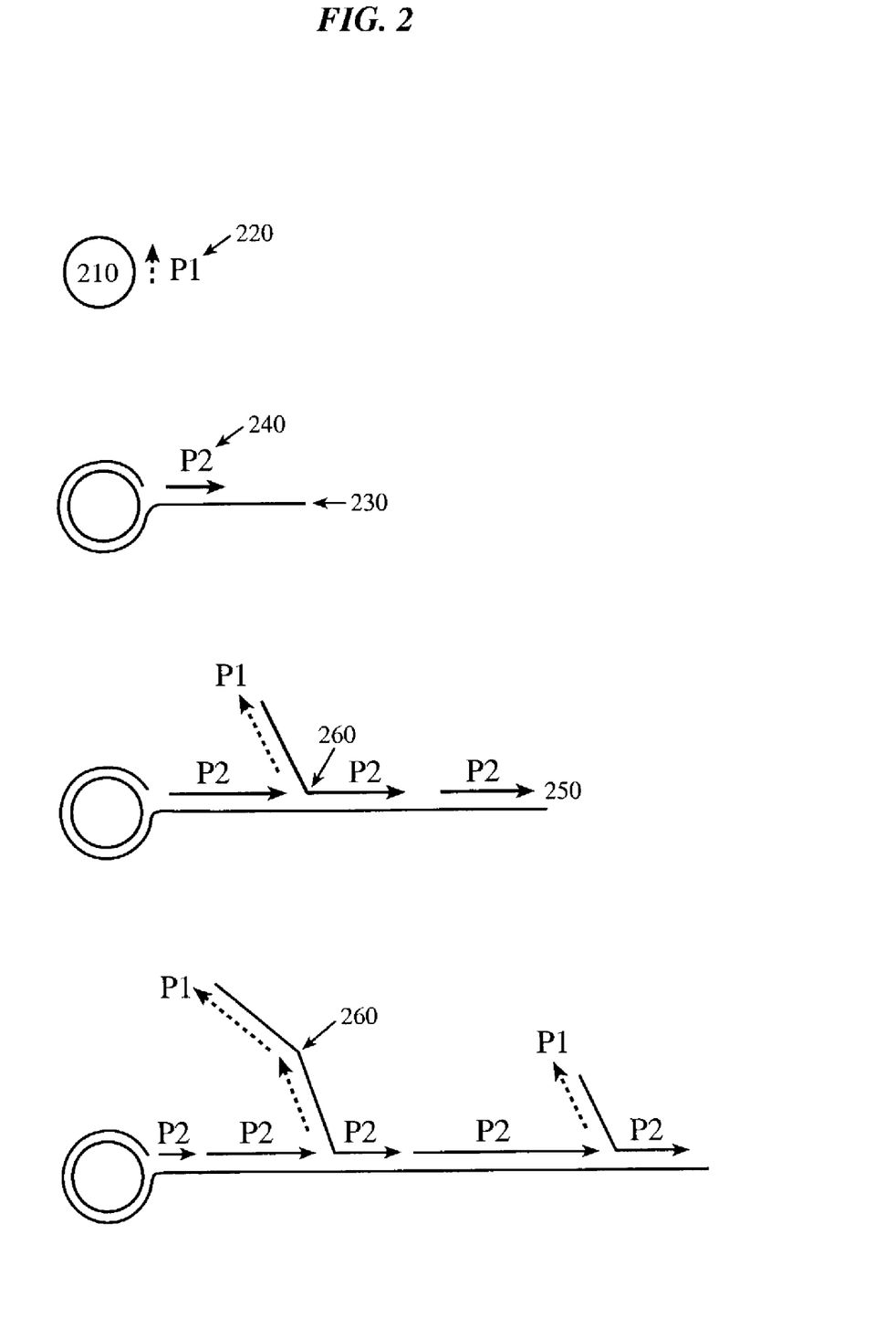
FIG. 2 illustrates a method for exponential rolling circle amplification (ERCA). A first primer 220 (P1) hybridizes to a single stranded circular nucleic acid template 210 and primes the RCA process. A second primer 240 (P2) hybridizes to another site within the amplified single-stranded sequence 230 and primes the formation of complementary strands 250. When a secondary amplification product 250 reaches the 5' end of an adjacent amplification product 250, strand displacement occurs, resulting in the formation of branch sites 260 in the amplification product 230, 250.

FIG. 2 illustrates an exemplary ERCA protocol (Lizardi et al., 1998). A circular, single-stranded DNA template 210 is allowed to hybridize to a first primer 220 (P1). A DNA polymerase 160, dNTP's and cofactors are added and the template 210 sequence is replicated to form an RCA amplification product 230. As the amplification product 230 extends around the circular template 210, it displaces the 5' end of the first primer 220 from the template 210, resulting in a single-stranded DNA molecule 230 that extends away from the circular template 210. This portion of the ERCA protocol (FIG. 2) is similar to the LRCA protocol (FIG. 1).

The main difference between LRCA and ERCA is in the addition of a second primer 240 (P2) that can bind to the complement of the template 210 sequence at a location away from the first primer 220. The second primer 240 can hybridize to the extended single-stranded amplification product 230. Addition of nucleotides to the 3' end of the second primer 240 results in the formation of a second strand amplification product 250 (FIG. 2). When the growing (3') end of a second strand 250 hits the 5' end of an adjacent second primer 240, that primer 240 and its attached second strand 250 are displaced from the initial amplification product 230. This results in the formation of branches 260 in the RCA amplification product 230, 250. Additional copies of the first primer 220 can bind to each of the branches 260, resulting in further amplification of the signal detectable from the target biomolecule 130. The net result of ERCA is a highly branched amplification product 230, 250 that can provide for exponential signal amplification.

ERCA provides an amplification factor of about $10^9$, or about $10^5$ greater amplification than is observed with LRCA. However, ERCA is generally unsuited for biomolecule 130 detection by hybridization with fluorescently tagged oligonucleotide probes 180. Following the ERCA process (FIG. 2), the majority of amplification product 230, 250 consists of double-stranded nucleic acid. There is no extended domain of unhybridized, single stranded amplification product 170, as obtained from LRCA. Thus, hybridization of tagged oligonucleotide probes 180 is much more difficult to per-form with ERCA than LRCA. Techniques that can separate the double-stranded ERCA amplification product 230, 250 into single strands (e.g., heating, low salt, pH, detergent) would make biomolecule 130 detection in a multiplex chip assay complicated and difficult. Although fluorescently tagged nucleotides could in principal be incorporated directly into the ERCA amplification product 230, 250, the efficiency of DNA polymerase 160 activity may be adversely affected by the presence of bulky fluorescent groups covalently attached to a substantial proportion of the dNTP precursors. Further, self-quenching of adjacent fluorescent dye molecules would reduce the signal strength. Self-quenching can also occur in LRCA if the tagged probes 180 are located too close to each other. Finally, the use of fluorescently tagged probes 180 adds to the expense and time required for biomolecule 130 detection.

Raman Detection

Raman Spectroscopy

In certain embodiments of the invention, rolling circle amplification may be used in combination with Raman detection to detect, identify and/or quantify target biomolecules 130. Any Raman detection modality known in the art may be used, including but not limited to surface enhanced Raman spectroscopy (SERS), surface enhanced resonance Raman spectroscopy (SERRS) normal Raman scattering, resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

In particular embodiments of the invention, a surface enhanced Raman technique, such as SERS or SERRS may be used to detect RCA amplification products 170, 230, 250, 330, 410. Such techniques rely on the enhancement of Raman signals for molecules adsorbed to roughened surfaces 140 of certain metals, such as silver, platinum, copper, aluminum or gold. In SERS and SERRS, the sensitivity of the Raman detection may be enhanced by a factor of $10^6$ or more. Methods of SERS detection of biomolecules 130, such as nucleic acids, are known in the art. Typically, such methods have utilized colloidal metal particles, such as aggregated silver nanoparticles, that were coated onto a substrate 140 and/or support (e.g., U.S. Pat. Nos. 5,306,403; 6,149,868; 6,174,677; 6,376,177). However, previous SERS or SERRS techniques for biomolecule 130 detection provided insufficient sensitivity and/or specificity. Additional details of Raman detection within the scope of the claimed methods, compositions and systems are provided below.

Raman Labels

In some embodiments of the invention, RCA amplification products 170, 230, 250, 330, 410 may be detected by direct detection of incorporated nucleotides. For example, purine nucleotides containing adenine or guanine moieties exhibit unique signals that can be detected by SERS or SERRS. In alternative embodiments, some of the nucleoside triphosphate precursors to be incorporated into the RCA amplification product 170, 230, 250, 330, 410 may be tagged with one or more Raman labels to facilitate their detection, identification and/or quantification. In other alternative embodiments, nucleoside triphosphate precursors may be covalently modified with a reactive group, such as sulfhydryl, amino, carboxyl, maleimide, biotin and/or other reactive moieties known in the art. After incorporation into an RCA amplification product 170, 230, 250, 330, 410, the modified nucleotides may be tagged with one or more Raman labels, designed to covalently or non-covalently bind to the reactive groups. Another method to incorporate Raman labels would be to conjugate the labels with oligonucleotide probes 180 that have sequences complementary to the RCA amplification product 170, 230, 250, 330, 410 and hybridize the oligonucleotide 180 to the RCA product 170, 230, 250, 330, 410. Such hybridization techniques are simplified where the RCA protocol produces a primarily single stranded product 170, 330. Such post-amplification modifications may be used, for example, where the presence of bulky Raman labels on the nucleoside triphosphate precursors might interfere with DNA polymerase 160 activity.

A variety of Raman labels of use for detecting biomolecules 130 are known in the art (e.g., U.S. Pat. Nos. 5,306,403; 6,002,471; 6,174,677) and any such known Raman label may be used. Non-limiting examples of labels that could be used for Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. These and other Raman labels may be obtained from commercial sources (e.g., Molecular Probes, Eugene, Oreg.).

Polycyclic aromatic compounds in general may function as Raman labels, as is known in the art. Other labels that may be of use for particular embodiments of the invention include cyanide, thiol, chlorine, bromine, methyl, phosphorus and sulfur groups. In certain embodiments of the invention, carbon nanotubes may be of use as Raman labels.

Labels may be attached directly to the nucleic acids or may be attached via various linker compounds. Alternatively, nucleotide precursors that are covalently attached to Raman labels may be purchased from standard commercial sources (e.g., Roche Molecular Biochemicals, Indianapolis, Ind.; Promega Corp., Madison, Wis.; Ambion, Inc., Austin, Tex.; Amersham Pharmacia Biotech, Piscataway, N.J.). Raman labels that contain reactive groups designed to covalently react with other molecules, such as nucleotides or nucleic acids, are commercially available (e.g., Molecular Probes, Eugene, Oreg.). Methods for preparing labeled nucleotides and incorporating them into nucleic acids are known (e.g., U.S. Pat. Nos. 4,962,037; 5,405,747; 6,136,543; 6,210,896).

Raman Detection Units

A variety of detection units of potential use in Raman spectroscopy are known in the art and any known Raman detection unit may be used. A non-limiting example of a Raman detection unit is disclosed in U.S. Pat. No. 6,002,471. In this example, the excitation beam is generated by either a Nd:YAG laser at 532 nm (nanometer) wavelength or a Ti:sapphire laser at 365 nm wavelength. Pulsed laser beams or continuous laser beams may be used. The excitation beam passes through confocal optics and a microscope objective, and may be focused onto a substrate 140 containing attached biomolecule targets 130. Raman emission light from the RCA amplification products 170, 230, 250, 330, 410 may be collected by the microscope objective and the confocal optics, coupled to a monochromator for spectral dissociation. The confocal optics may include a combination of dichroic filters, barrier filters, confocal pinholes, lenses, and mirrors for reducing the background signal. Standard full field optics can be used as well as confocal optics. The Raman emission signal may be detected by a Raman detector. The detector may include an avalanche photodiode interfaced with a computer for counting and digitization of the signal. Where arrays of target biomolecules 130 are to be analyzed, the optical detection system may be designed to detect and localize Raman signals to specific locations on a chip or grid. For example, emitted light may be channeled to a CCD (charge coupled device) camera or other detector that is capable of simultaneously measuring light emission from multiple pixels or groups of pixels within a detection field.

Alternative examples of Raman detection units are disclosed, for example, in U.S. Pat. No. 5,306,403, including a Spex Model 1403 double-grating spectrophotometer equipped with a gallium-arsenide photomultiplier tube (RCA Model C31034 or Burle Industries Model C3103402) operated in the single-photon counting mode. The excitation source is a 514.5 nm line argon-ion laser from SpectraPhysics, Model 166, and a 647.1 nm line of a krypton-ion laser (Innova 70, Coherent).

Alternative excitation sources include, but are not limited to, a nitrogen laser (Laser Science Inc.) at 337 nm and a helium-cadmium laser (Liconox) at 325 nm (U.S. Pat. No. 6,174,677). The excitation beam may be spectrally purified with a bandpass filter (Corion) and may be focused on a substrate 140 using a 6× objective lens (Newport, Model L6X). The objective lens may be used to both excite the RCA amplification products 170, 230, 250, 330, 410 and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include, but are not limited to, an ISA HR-320 spectrograph equipped with a red-enhanced intensified charge-coupled device (RE-ICCD) detection system (Princeton Instruments). Other types of detectors may be used, such as charged injection devices, photodiode arrays or phototransistor arrays.

Nanoparticles of Raman Active Metals

In certain embodiments of the invention, Raman active metal particles, such as gold or silver nanoparticles, may be added to a substrate 140 containing attached RCA amplification products 170, 230, 250, 330, 410 to facilitate Raman signal detection by SERS or SERRS. For example, a colloidal nanoparticle slurry could be flowed over a biomolecule 130 array, at a nanoparticle density sufficient to provide SERS or SERRS signals from each biomolecule 130 location on the array. Alternatively, nanoparticles could be deposited directly on a biomolecule 130 array or other substrate 140 at a density sufficient to provide SERS or SERRS signals from each location. Although any nanoparticle density that provides for surface enhanced Raman signals may be used, in particular embodiments of the invention a particle density providing between 1 nm to 20 nm separation between adjacent nanoparticles or nanoparticle aggregates may be used. In some embodiments of the invention, nanoparticles may be formed by direct interaction with RCA amplification products 170, 230, 250, 330, 410. For example, an array containing attached RCA amplification products 170, 230, 250, 330, 410 could be treated with an aldehyde, such as glutaraldehyde (e.g., Keren et al., *Science* 297:72–75). The aldehyde groups can covalently modify nucleic acids, making them reducing agents for metal salts. The modified nucleic acids may be exposed to a metal salt solution containing metal cations, for example a silver nitrate solution (containing between about 0.2 to 2.0 M $AgNO_3$). The $Ag^+$ cations will be reduced by the aldehyde groups, producing silver nanoparticles that are closely associated with the RCA amplification products 170, 230, 250, 330, 410.

Alternative methods of preparing nanoparticles are known (e.g., U.S. Pat. Nos. 6,054,495; 6,127,120; 6,149,868; Lee and Meisel, *J. Phys. Chem.* 86:3391–3395, 1982). Nanoparticles may be produced in the form of nanoprisms (Jin et al., "Photoinduced conversion of silver nanospheres to nanoprisms," *Science* 294:1901, 2001). Nanoparticles may also be obtained from commercial sources (e.g., Nanoprobes Inc., Yaphank, N.Y.; Polysciences, Inc., Warrington, Pa.).

In certain embodiments of the invention, the nanoparticles may be random aggregates of nanoparticles (colloidal nanoparticles). In other embodiments of the invention, nanoparticles may be cross-linked to produce particular aggregates of nanoparticles, such as dimers, trimers, tetramers or other aggregates. Certain alternative embodiments of the invention may use heterogeneous mixtures of aggregates of different size, while other alternative embodiments may use homogenous populations of nanoparticle aggregates. In certain embodiments of the invention, aggregates containing a selected number of nanoparticles (dimers, trimers, etc.) may be enriched or purified by known techniques, such as ultracentrifugation in sucrose gradient solutions.

Methods of cross-linking nanoparticles are known in the art (see, e.g., Feldheim, "Assembly of metal nanoparticle arrays using molecular bridges," The Electrochemical Society Interface, Fall, 2001, pp. 22–25). Reaction of gold nanoparticles with linker compounds bearing terminal thiol or sulfhydryl groups is known (Feldheim, 2001). In some embodiments of the invention, nanoparticles may be cross-linked to each other to form aggregates. In other embodiments, the nanoparticles could potentially be attached directly to the RCA amplification products 170, 230, 250, 330, 410. Modified nanoparticles suitable for cross-linking to other nanoparticles or to RCA amplification products 170, 230, 250, 330, 410 are commercially available, such as the Nanogold® nanoparticles from Nanoprobes, Inc. (Yaphank, N.Y.). Nanogold® nanoparticles may be obtained with either single or multiple maleimide, amine or other groups attached per nanoparticle. The Nanogold® nanoparticles are also available in either positively or negatively charged form to facilitate manipulation of nanoparticles in an electric field, allowing manipulation of nanoparticles by electrokinetic or other processes.

Biomolecule Arrays

In certain embodiments of the invention, the target biomolecules 130 and/or RCA amplification products 170, 230, 250, 330, 410 may be attached to a substrate 140, array and/or chip. As used herein, the terms "chip," "substrate" 140 and "array" are used interchangeably. Methods for manufacture and use of biomolecule 130 chips are known in the art and any such known method may be used (e.g., U.S. Pat. Nos. 5,143,854; 5,874,219; 6,040,138; 6,124,102; 6,203,989; 6,225,625; 6,252,236; 6,399,365; 6,410,229; 6,416,952). Different methods may be used to create biomolecule 130 chips, including synthesis of biomolecules 130 or ligands for biomolecules 130 directly on a chip surface 140. Alternatively, biomolecules 130 or their ligands may be synthesized or purified and then attached to a chip surface 140. Many alternative methods are known, such as attaching a first, capture antibody 120 to a chip, using the first antibody 120 to bind to and immobilize a target biomolecule 130, then adding a second tagged antibody 120 to detect the biomolecule 130. Such a "sandwich" assay system could be used in the claimed methods, with the second antibody 120 covalently attached to an oligonucleotide primer 110, 220 as in the immunoRCA protocol illustrated in FIG. 1. In related embodiments of the invention where a ligand for a biomolecule 130 is attached to a chip, the ligand may then be used to bind a biomolecule 130. The ligand-biomolecule 130 complex may be detected by binding of a second ligand, such as an antibody 120, that binds to a different domain of the biomolecule 130. Various chip substrates 140 that may be used to create biomolecule 130 arrays are commercially available (e.g., NanoChip™ System, Nanogen, San Diego, Calif.; GeneChip®, Affymetrix, Santa Clara, Calif.) and may be used.

Attachment of Biomolecules to a Substrate

In various embodiments of the invention, biomolecules 130 may be immobilized by attachment to a solid substrate 140. Biomolecules 130 may be immobilized by a variety of known methods involving either non-covalent or covalent attachment. For example, immobilization may be achieved by coating a solid substrate 140 with streptavidin or avidin and binding of a biotin-conjugated biomolecule 130. Immobilization may also occur by coating a silicon, quartz, PDMS (polydimethyl siloxane) or other solid substrate 140 with poly-L-Lys or aminosilane, followed by covalent attachment of either amino- or sulfhydryl-containing biomolecules 130 using bifunctional cross linking reagents. Bifunctional cross-linking reagents of potential use include glutaraldehyde, bifunctional oxirane, ethylene glycol diglycidyl ether, and carbodiimides, such as 1-ethyl-3-(3-dimethylaminopropyl) carbodiimide.

In alternative embodiments of the invention, substrates 140 to be attached to biomolecules 130 may be first patterned using standard photolithography and etching techniques to create microscale or nanoscale attachment areas for biomolecules 130. For example, substrates 140 may be coated with a thin layer of gold metal. The gold may be directly conjugated to sulfhydryl residues of biomolecules 130. Alternatively, a linking group such as mercaptobenzoic acid and/or mercaptohexadecanoic acid may be used to form monolayers on the gold patches (e.g. Liu and Amro, Proc. Natl. Acad. Sci. USA, 99:5165–70, 2002). In this case, the mercapto moieties bind to the gold patches, allowing attachment of biomolecules 130, for example by carbodiimide catalyzed covalent bond formation between acidic moieties on the monolayer and amino groups on the biomolecules 130. Alternatively, acid-acid dimer hydrogen bonding or acid anhydride bond formation can occur between carboxyl groups on the monolayer and acidic residues on the biomolecule 130.

Immobilization may take place by direct covalent attachment of acidic residues on biomolecules 130 to chemically modified substrates 140, for example acid treated silicon. The covalent bond between the biomolecule 130 and the solid substrate 140 may be formed by condensation with a cross-linking reagent.

Biomolecules 130 may be bound to a substrate 140 by first silanizing the substrate 140, then activating with carbodiimide or glutaraldehyde. Alternative procedures may use reagents such as 3-glycidoxypropyltrimethoxysilane or aminopropyltrimethoxysilane (APTS) with biomolecules 130 linked via amino linkers. Other methods of immobilizing biomolecules 130 are known and may be used. In certain embodiments of the invention a capture oligonucleotide may be bound to a substrate 140. The capture oligonucleotide can hybridize with a specific sequence of a nucleic acid biomolecule 130.

The type of substrate 140 to be used for immobilization of the biomolecule 130 is not limited. In various embodiments, the immobilization substrate 140 may be quartz, PDMS, silicon, silicon oxide, silicon dioxide, silicon nitride, germanium, or any other substrate 140 known in the art.

Micro-Electro-Mechanical Systems (MEMS)

In some embodiments of the invention, substrates 140, arrays and/or chips containing attached biomolecules 130 and/or RCA amplification products 170, 230, 250, 330, 410 may be incorporated into a larger apparatus and/or system, such as a microfluidic system. In certain embodiments, the substrate 140 may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate 140 (e.g., Voldman et al., Ann. Rev. Biomed. Eng. 1:401–425, 1999). The sensor components of MEMS may be used to measure mechanical, thermal, biological, chemical, optical and/or magnetic phenomena, such as Raman emission signals. The electronics may process the information from the sensors and control actuator components such pumps, valves, heaters, coolers, filters, etc. thereby controlling the function of the MEMS.

The electronic components of MEMS may be fabricated using integrated circuit (IC) processes (e.g., CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate 140, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, e.g., Craighead, Science 290:1532–36, 2000.)

In some embodiments of the invention, one or more substrates 140, arrays and/or chips may be connected to various fluid filled compartments, such as microfluidic channels, nanochannels and/or microchannels. These and other components of an apparatus or system may be formed as a single unit, for example in the form of a chip as known in semiconductor chips and/or microcapillary or microfluidic chips. Alternatively, a substrate 140, array and/or chip may be formed as a discrete unit and then attached to other components of an apparatus or system. Any materials known for manufacture of substrates 140, arrays or chips may be used, including but not limited to silicon, silicon dioxide, silicon nitride, polydimethyl siloxane (PDMS), polymethylmethacrylate (PMMA), plastic, glass, quartz, etc.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate 140, followed by reactive ion etching. Various forms of microfabricated chips are commercially available from, e.g., Caliper Technologies Inc. (Mountain View, Calif.) and ACLARA BioSciences Inc. (Mountain View, Calif.).

In certain embodiments of the invention, part or all of an apparatus or system may be selected to be transparent to electromagnetic radiation at the excitation and emission frequencies used for Raman spectroscopy, such as glass, silicon, quartz or any other optically clear material. For fluid-filled compartments that may be exposed to various biomolecules 130, such as proteins, peptides, nucleic acids, nucleotides and the like, the areas exposed to such molecules may be modified by coating, for example to transform a hydrophobic to a hydrophilic area and/or to decrease adsorption of molecules. Modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Biomolecule Detection Utilizing SERS and RCA

The rolling circle amplification techniques may be combined with SERS or SERRS to detect, identify and/or quantify a wide variety of biomolecules 130. In embodiments of the invention where the biomolecule 130 to be detected is a nucleic acid, polynucleotide or oligonucleotide, rolling circle amplification is straightforward. A circular DNA template 150, 210, 310 is designed to include sequences that will hybridize to the 3' end of the target nucleic acid 130. Appropriate precursors, enzymes and cofactors are added and an RCA amplification product 170, 230, 250, 330, 410 is formed. Depending on whether LRCA or ERCA is performed, the result will be a single-stranded amplification product 170, 330 or a branched, double-stranded amplification product 230, 250, 410. In the case of ERCA, fluorescent detection using labeled oligonucleotide probes 180 is not feasible. With either LRCA or ERCA, Raman detection may be used to detect, identify and/or quantify the target biomolecule 130.

In alternative embodiments of the invention, the target biomolecule 130 may be a peptide, protein, glycoprotein, polysaccharide, glycolipid or other molecule for which a peptide or protein ligand, such as an antibody 120, may be used as a binding and detection agent. In such cases, some variant of immunoRCA may be used with either LRCA or ERCA. Monoclonal antibodies 120, polyclonal antibodies 120, antibody 120 fragments (e.g., FAb fragments), humanized antibodies 120, single-chain antibodies 120 and chimeric antibodies 120 may be purchased from commercial sources or prepared by known techniques (e.g., Harlow and Lane, *Antibodies: A Laboratory* Manual, Cold Spring Harbor Press, Cold Spring Harbor, N.Y., 1988). The 5' end of an oligonucleotide primer 110, 220 may be attached to an antibody 120 or other protein or peptide ligand using known methods (e.g., Schweitzer et al., 2000; Schweitzer et al., 2002).

A variety of methods for attaching primers 110, 220 to antibodies 120 or other proteins are known. For example, a sulfhydryl residue may be covalently cross-linked with a acrydite modified primer 110, 220. Sulhydryl residues may also be cross-linked with 5' amino labeled primers 110, 220 using N-succinimidyl-4-maleimidobutyrate as a cross-linking reagent. The amino groups of lysine, arginine or N-terminal amino acids may be cross-linked to thiolated primers 110, 220 using the same cross-linker. Alternatively, water-soluble carbodiimides may be used to crosslink 5' carboxylated primers 110, 220 to amino moieties of proteins. Hydroxyl groups (e.g., serine, threonine) may be crosslinked to primers 110, 220 containing 5' amino groups by reaction with $IO_4$ and sodium borohydride. Many alternative methods of crosslinking primers 110, 220 to proteins or peptides are known and may be used.

Figure 3:
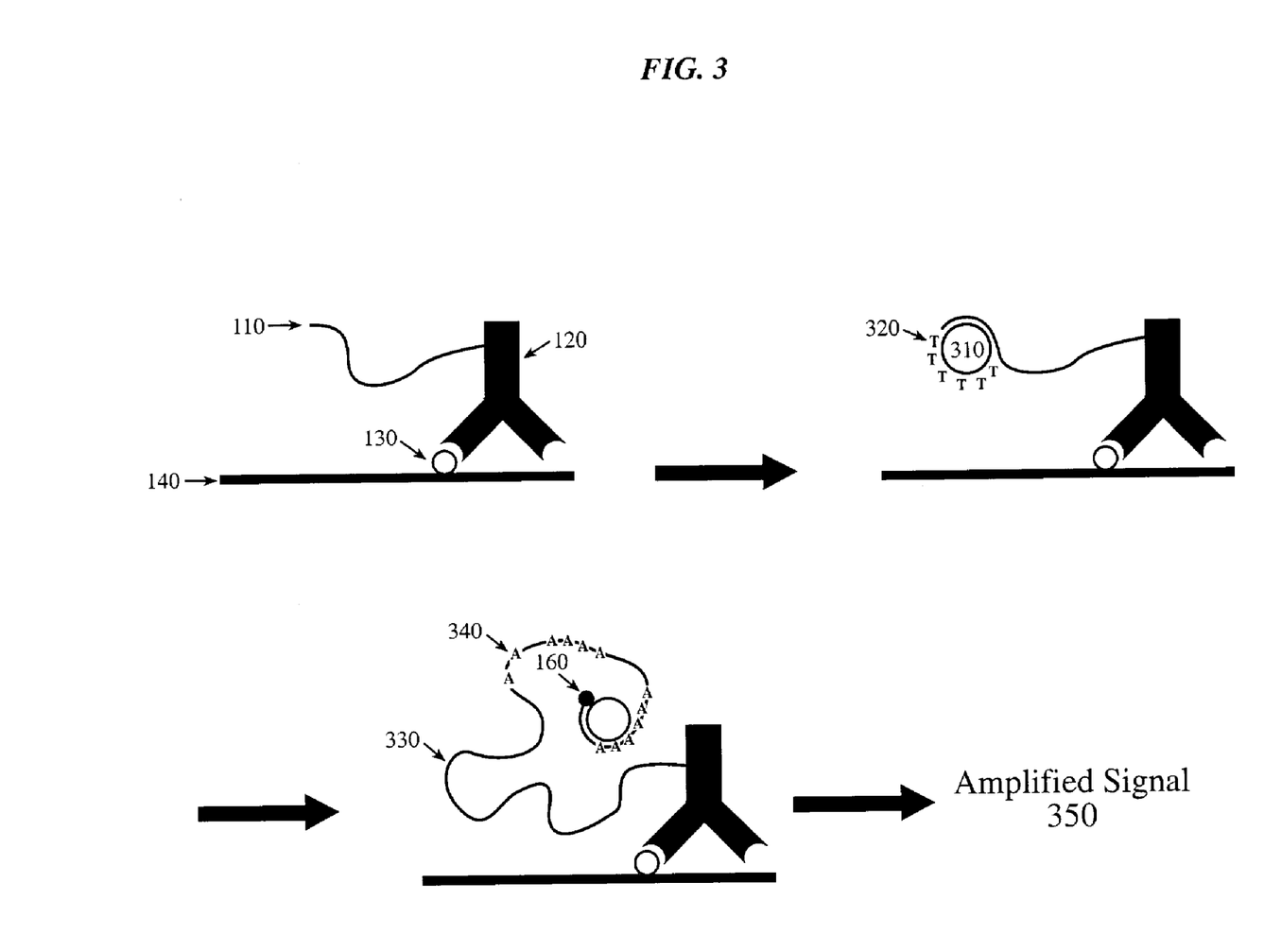
FIG. 3 illustrates an exemplary method of SERS detection of LRCA products 330 containing polyadenylate 340 residues.

An exemplary embodiment of the invention is illustrated in FIG. 3, which shows Raman detection in combination with LRCA. As in FIG. 1, a target biomolecule 130 may be attached to a substrate 140. Any target biomolecule 130 for which an antibody 120 or other protein, peptide or nucleic acid ligand is available may be detected, so long as the ligand binds with relatively high specificity to the target 130 of interest. In the case of an antibody 120, peptide or protein ligand, the ligand, exemplified by an antibody 120 in FIG. 3, would be conjugated to an oligonucleotide primer 110, as in FIG. 1.

Several variations may be utilized for Raman detection. In the exemplary embodiment illustrated in FIG. 3, a circular DNA template 310 that is designed to contain one or more polythymidine 320 (T) residues is hybridized to the oligonucleotide primer 110. Upon addition of DNA polymerase 160, dNTP's and cofactors, an elongated single-stranded RCA amplification product 330 is formed, containing multiple polyadenylate 340 (A) residues. The polyadenylates 340 may be directly detected by SERS or SERRS. Alternatively, oligonucleotide probes 180 designed to have unique Raman signatures could be hybridized to the LRCA amplification product 330 and detected.

Using the Raman detection unit disclosed in Example 1 below, SERS signals have been detected in samples containing as few as 60 molecules of adenine (Example 1). In contrast to fluorescent detection, where a high concentration of a fluorescent moiety may lead to self-quenching, the incorporation of adenine into nucleic acids produces an enhanced signal rather than self-quenching. Molecules of polyadenylate 340 containing 30 contiguous adenine residues $(A)_{30}$ produced a SERS signal equivalent to ten times the same number of molecules of deoxyadenosine-5'-monophosphate (dAMP) (data not shown). A single-stranded LRCA amplification product 330 with incorporated polyadenylates 340 may contain up to $10^5$ adenine residues, giving a very strong amplified SERS signal 350 that would allow detection of single copies of a target biomolecule 130.

The same methods may be used with ERCA (FIG. 4), with even greater signal amplification. The protocol starts with a biomolecule 130 which may be attached to a substrate 140. In the non-limiting example of FIG. 4, the biomolecule 130 binds with an antibody 120 that is conjugated to an oligonucleotide primer 110. As in FIG. 3, a single-stranded DNA template 310 containing one or more polythymidine residues 320 is hybridized to the primer 110. An ERCA protocol, as exemplified in FIG. 2, is followed, resulting in formation of a highly branched ERCA amplification product 410 containing multiple polyadenylate 420 residues. The polyadenylate 420 residues in the ERCA product 410 may be directly detected by Raman techniques, such as SERS or SERRS. Alternatively, the amplification product 410 may incorporate one or more Raman labels to facilitate detection, identification and/or quantification. As discussed above, Raman labels could be incorporated directly into the amplification product 410 by using nucleotide precursors covalently tagged with Raman labels. Alternatively, Raman labels could be added to the amplification product 410 after it is synthesized. In any case, a greatly amplified Raman signal 430 will be produced.

Figure 4:
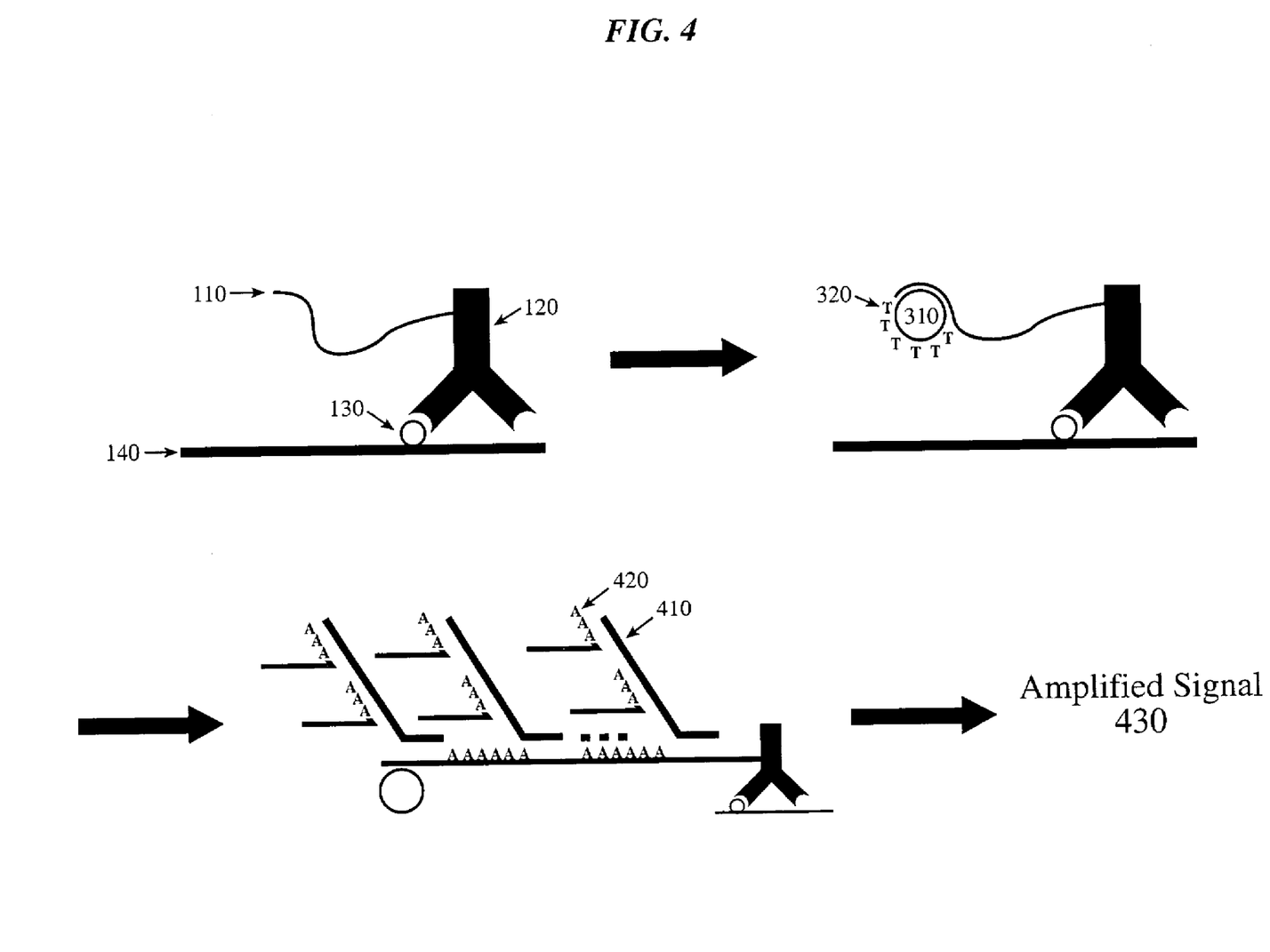
FIG. 4 illustrates an exemplary method of SERS detection of ERCA products 410 containing polyadenylate 420 residues.

The ERCA protocol results in a Raman signal amplification of $10^9$ or more. In combination with the signal enhancement produced by the multiple polyadenylate 420 residues, the combination of ERCA with SERS or SERRS detection would allow ultra-high sensitivity detection of biomolecules 130, down to the single molecule level. These methods exhibit significantly greater sensitivity compared to standard methods of fluorescent detection of RCA amplification products 170, 230, 250, 330, 410. Compared to fluorescence detection of LRCA amplification products 170, 330, SERS detection of ERCA amplification products 230, 250, 410 should provide at least a three order of magnitude increase in signal intensity.

With either RCA protocol, the amount of one or more target biomolecules 130 in a sample may be quantified by Raman spectroscopy, using any known method of quantification. For example, quantification may occur by detecting the intensity of emitted Raman signals and spot counting. In spot counting, a narrow laser excitation beam (less than 1 µm in diameter) may be used to scan a surface or substrate 140 to identify the number of individual amplification events and how many kinds of amplification events are associated with a given target 130. The spot counting method may avoid intensity variations caused by incomplete or inefficient DNA amplification or colloid aggregation.

EXAMPLES

Example 1

Detection of RCA Products by SERS

Silver Nanoparticle Formation

Silver nanoparticles used for SERS detection were produced by known methods (Lee and Meisel, 1982). Eighteen milligrams of $AgNO_3$ were dissolved in 100 mL (milliliters) of distilled water and heated to boiling. Ten mL of a 1% sodium citrate solution was added drop-wise to the $AgNO_3$ solution over a 10 min period. The solution was kept boiling for another hour. The resulting silver colloid solution was cooled and stored.

Raman Detection Unit

The excitation beam was generated by a titanium:sapphire laser (Tsunami by Spectra-Physics) at a near-infrared wavelength (750~950 nm) or a galium aluminum arsenide diode laser (PI-ECL series by Process Instruments) at 785 nm or 830 nm. Pulsed laser beams or continuous beams may be used. The excitation beam was reflected by a dichroic mirror (holographic notch filter by Kaiser Optical or an interference filter by Chroma or Omega Optical) into a collinear geometry with the collected beam. The reflected beam passed through a microscope objective (Nikon LU series), and was focused onto a substrate 140 where target biomolecules 130 were located. The Raman scattered light was collected by the same microscope objective, and passed through the dichroic mirror to a Raman detector. The Raman detector comprised a focusing lens, a spectrograph, and an array detector. The focusing lens focused the Raman scattered light through the entrance slit of a spectrograph. The spectrograph (RoperScientific) comprised a grating that dispersed the light by its wavelength. The dispersed light was imaged onto an array detector (back-illuminated deep-depletion CCD camera by RoperScientific). The array detector was connected to a controller circuit, which was connected to a computer for data transfer and control of the detector function.

SERS Detection of Adenine

One mL of silver colloid solution was diluted with 2 mL of distilled water. The diluted silver colloid solution (160 µL) (microliters) was mixed with 20 µL of a 10 nM (nanomolar) adenine solution and 40 µL of LiCl (0.5 molar) on an aluminum tray. The LiCl acted as a Raman enhancing agent for adenine. The final concentration of adenine in the sample was 0.9 nM, in a detection volume of about 100 to 150 femtoliters, containing an estimated 60 molecules of adenine. The Raman emission spectrum was collected using an excitation source at 785 nm excitation, with a 100 millisecond collection time.

Figure 5:
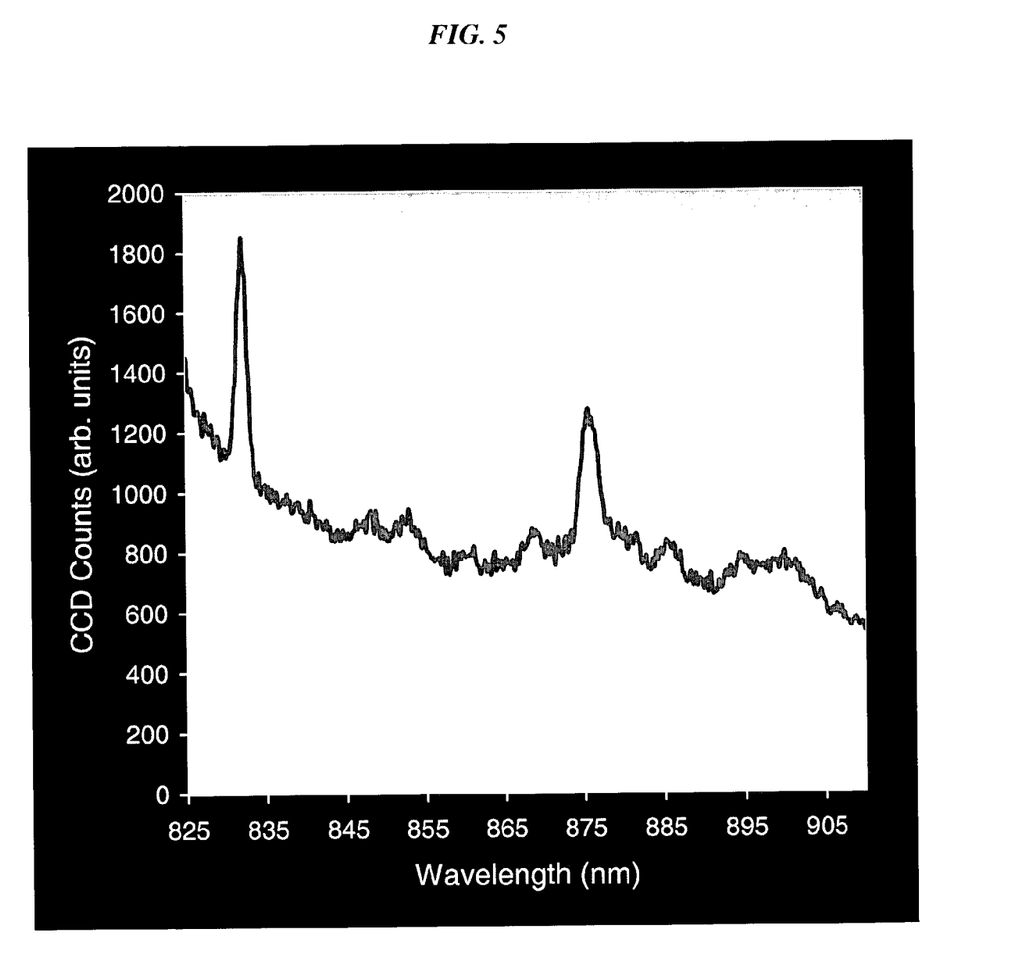
FIG. 5 shows the SERS detection of a 0.9 nM (nanomolar) solution of adenine. The detection volume was 100 to 150 femtoliters, containing an estimated 60 molecules of adenine.

As shown in FIG. 5, this procedure demonstrated the sensitive detection of 60 molecules of adenine, with strong emission peaks detected at about 833 nm and 877 nm. These results demonstrate that SERS can be used for the sensitive detection of adenine, a component of RCA amplification products 170, 230, 250, 330, 410.

Rolling Circle Amplification

The utility of SERS detection for identification of RCA amplification products 170, 230, 250, 330, 410 was demonstrated. One picomole (pmol) of an RCA primer 110, 220 was added to 0.1 pmol of circular, single-stranded M13 DNA template 150, 210, 310. The mixture was incubated with 1×T7 polymerase 160 buffer (20 mM (millimolar) Tris-HCl, pH 7.5, 10 mM $MgCl_2$, 1 mM dithiothreitol), 0.5 mM dNTPs and 2.5 units of T7 DNA polymerase 160 for 2 hours at 37° C., resulting in formation of an RCA product 170, 230, 250, 330, 410. A negative control was prepared by mixing and incubating the same reagents without the DNA polymerase 160.

SERS Detection of RCA Product

One µL of the RCA product 170, 230, 250, 330, 410 and 1 µL of the negative control sample were separately spotted on an aluminum tray and air-dried. Each spot was rinsed with 5 µL of 1×PBS (phosphate buffered saline). The rinse was repeated three times and the aluminum tray was air-dried after the final rinse.

Figure 6A:
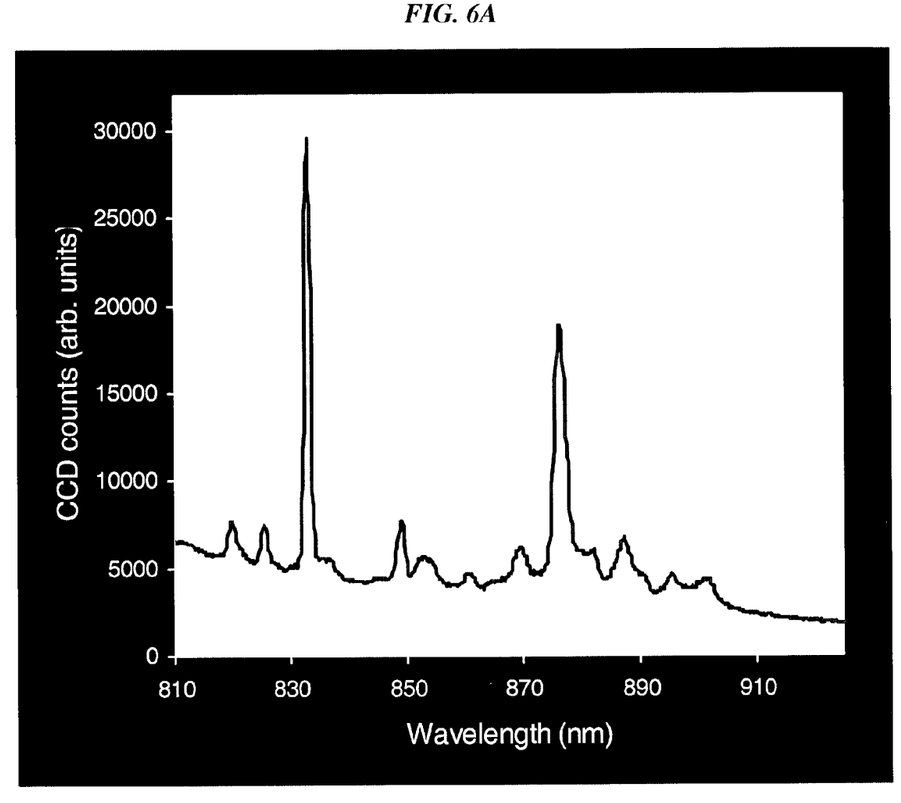
FIG. 6A shows the SERS detection of a rolling circle amplification product 170, 230, 250, 330, 410, using a single-stranded, circular M13 DNA template 150, 210, 310.
Figure 6B:
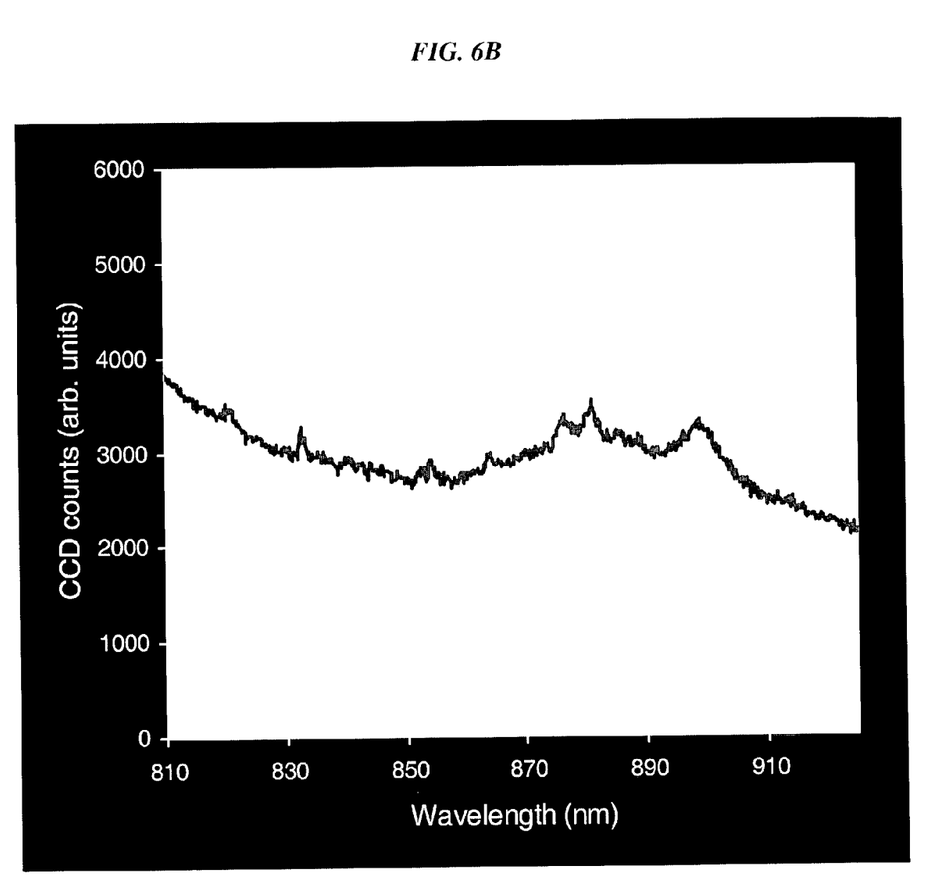
FIG. 6B shows a negative control in the absence of DNA polymerase 160. The absorbance scale has been changed from FIG. 6B to magnify the baseline.

One milliliter of silver colloid solution prepared as above was diluted with 2 mL of distilled water. Eight microliters of the diluted silver colloid solution was mixed with 2 µL of 0.5 M LiCl and added to the RCA product 170, 230, 250, 330, 410 spot on the aluminum tray. The same solution was added to the negative control spot. The Raman signals were collected as disclosed above. The results are shown in FIG. 6A and FIG. 6B. As demonstrated in FIG. 6A, an RCA product 170, 230, 250, 330, 410 is easily detectable by SERS, with emission peaks at about 833 and 877 nm. Under the conditions of this protocol, with an LiCl enhancer, the signal strength from the adenine moieties is much stronger than those for guanine, cytosine and thymine. The negative control (FIG. 6B) shows that the Raman signal was specific for the RCA product 170, 230, 250, 330, 410, as no signal was observed in the absence of amplification. As only one primer 110, 220 was added, FIG. 6 illustrates that SERS works to detect LRCA amplification products 170, 330. Because of the greater fold-amplification afforded with ERCA, the ERCA amplification products 230, 250, 410 should show even stronger signals. These results demonstrate that LRCA and ERCA can be used in combination with SERS detection to identify target biomolecules 130.

All of the METHODS, COMPOSITIONS and SYSTEMS disclosed and claimed herein can be made and used without undue experimentation in light of the present disclosure. It will be apparent to those of skill in the art that variations may be applied to the METHODS, COMPOSITIONS and SYSTEMS described herein without departing from the concept, spirit and scope of the claimed subject matter. More specifically, it will be apparent that certain agents that are related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) attaching one or more target biomolecules to a substrate;
   b) using a first primer to produce one or more rolling circle amplification (RCA) products;
   c) hybridizing a circular, single stranded DNA template to the first primer, the template containing one or more polythymidine residues;
   d) adding a solution comprising LiCl;
   e) detecting each amplification product by Raman spectroscopy;
   f) identifying one or more target biomolecules by the presence of one or more amplification products, wherein the LiCl enhances the Raman emission from polyadenine comprising the resulting RCA product.

2. The method of claim 1, wherein each amplification product is attached to a target biomolecule.

3. The method of claim 1, wherein the target biomolecules are nucleic acids, polynucleotides or oligonucleotides.

4. The method of claim 3, wherein the nucleic acids are RNA or DNA.

5. The method of claim 3, wherein the first primer comprises the 3' end of the target biomolecules.

6. The method of claim 3, wherein the first primer hybridizes to the target biomolecules.

7. The method of claim 1, wherein the target biomolecules are peptides, polypeptides or proteins.

8. The method of claim 7, wherein the target biomolecules bind to one or more ligands.

9. The method of claim 8, wherein the ligands are conjugated to said first primer.

10. The method of claim 9, wherein the ligands are antibodies, antibody fragments, single chain antibodies, humanized antibodies or chimeric antibodies.

11. The method of claim 1, wherein the rolling circle, amplification is linear RCA (LRCA) or exponential RCA (ERCA).

12. The method of claim 1, wherein the Raman spectroscopy is surface enhanced Raman spectroseopy (SERS) or surface enhanced resonance Raman spectroscopy (SERRS).

13. The method of claim 1, further comprising comparing emissions obtained from a test sample with a negative control sample.

14. The method of claim 11, wherein the rolling circle amplification is ERCA, further comprising adding a second primer which hybridizes to the one or more rolling circle amplification (RCA) products.

15. The method of claim 1, further comprising exposing the amplification products to a silver colloid solution.

16. The method of claim 1, further comprising generating metal nanoparticles by a reaction between aqueous metal salts and the amplification products.

17. The method of claim 16, further comprising treating the amplification products with an aldehyde to form a reducing agent.

18. The method of claim 16, wherein the metal salts comprise $Ag^+$, $Cu^+$, $Cu^{2+}$, $Au^+$, $Au^{3+}$, $Pd^{2+}$, $Pd^{4+}$ or $Al^{3+}$.

19. The method of claim 1, further comprising incorporating one or more Raman labels into said amplification products.

20. The method of claim 1, further comprising quantifying the amount of one or more target biomolecules.

* * * * *

UNITED STATES PATENT AND TRADEMARK OFFICE
CERTIFICATE OF CORRECTION

PATENT NO. : 7,192,703 B2  Page 1 of 1
APPLICATION NO. : 10/367071
DATED : March 20, 2007
INVENTOR(S) : Sun et al.

It is certified that error appears in the above-identified patent and that said Letters Patent is hereby corrected as shown below:

On the Title page, in Item (56), under "Other Publications", in column 2, line 22, delete "Enchanced" and insert -- Enhanced --, therefor.

In column 16, line 11, in Claim 10, delete "single chain" and insert -- single-chain --, therefor.

In column 16, line 13, in Claim 11, delete "circle," and insert -- circle --, therefor.

In column 16, line 17, in Claim 12, delete "spectroseopy" and insert -- spectroscopy --, therefor.

Signed and Sealed this

Nineteenth Day of August, 2008

JON W. DUDAS
*Director of the United States Patent and Trademark Office*